US005741913A

United States Patent [19]
Oda et al.

[11] Patent Number: 5,741,913
[45] Date of Patent: Apr. 21, 1998

[54] PROCESS FOR PREPARING N-SUBSTITUTED MALEIMIDES

[75] Inventors: Masasuke Oda, Hyogo; Toshimitsu Noda, Osaka, both of Japan

[73] Assignee: Daihachi Chemical Industry Co., Ltd., Osaka, Japan

[21] Appl. No.: 790,312

[22] Filed: Jan. 28, 1997

[30] Foreign Application Priority Data

Jun. 10, 1996 [JP] Japan ................................. 8-147266

[51] Int. Cl.$^6$ ................... C07D 207/448; C07D 207/452
[52] U.S. Cl. ................................. 548/548; 548/549
[58] Field of Search ........................ 548/548, 549

[56] References Cited

U.S. PATENT DOCUMENTS

| | | |
|---|---|---|
| 4,141,905 | 2/1979 | Becker et al. . |
| 4,180,508 | 12/1979 | Becker et al. . |
| 4,276,090 | 6/1981 | Becker et al. . |
| 4,980,483 | 12/1990 | Kita et al. . |
| 5,175,309 | 12/1992 | Tsumura et al. . |
| 5,306,828 | 4/1994 | Adda et al. . |

FOREIGN PATENT DOCUMENTS

| | | |
|---|---|---|
| 129125 | 12/1984 | European Pat. Off. . |
| 334497 | 9/1989 | European Pat. Off. . |
| 372922 | 6/1990 | European Pat. Off. . |
| 499959 | 8/1992 | European Pat. Off. . |
| 6011465 | 1/1985 | Japan . |
| 60-109562 | 6/1985 | Japan . |

OTHER PUBLICATIONS

Patent Abstracts of Japan, Japanese Patent Office, Publication No. 60109562 A., Jun. 1985.
Database WPIDS on STN, Derwent Information, Ltd., (London, UK), Accession No. 85-181184, JP 60-109562, abstract, 1985.

*Primary Examiner*—Michael G. Ambrose
*Attorney, Agent, or Firm*—Greenblum & Bernstein, P.L.C.

[57] ABSTRACT

A process for preparing N-substituted maleimide is disclosed, which includes reacting maleic anhydride with a primary amine using both a non-polar solvent and a protic polar solvent in the presence of an acid catalyst.

15 Claims, No Drawings

PROCESS FOR PREPARING N-SUBSTITUTED MALEIMIDES

BACKGROUND OF THE INVENTION

1. Field of the Invention

The present invention relates to a process of preparing N-substituted maleimides. The N-substituted maleimides are generally used in a number of fields as materials for medicines, agricultural chemicals, dyes or polymers, or intermediates thereof.

2. Description of Related Art

Various processes are known for preparing N-substituted maleimides. One of such processes, for example, is a conventional two-step reaction process in which a maleic acid monoamide is synthesized from maleic anhydride and a primary amine in the presence of a non-polar solvent and then is dehydrocyclized in the presence of an acid catalyst using a non-polar solvent or a non-protic polar solvent such as N,N-dimethylformamide (DMF) (see Japanese Unexamined Patent Publication No. Sho 60(1985)-109562). Another process is a conventional single-step reaction process in which maleic anhydride is reacted with a primary amine in the presence of an acid catalyst in an inert solvent with continuous supply of the primary amine under refluxing of the solvent and simultaneous removal of generated water out of the reaction system (see Japanese Unexamined Patent Publication No. Sho60(1985)-11465).

The above-mentioned processes can be recognized to be industrially useful. However, the inventors of the present invention have found that, in these processes, the materials and by-products often deposit on the inside of a reactor and the resultant blocking of a reaction pipe system lowers productive efficiency. The by-products sometimes block the inside of a condenser, and damages or stops the function of a water separator. These problems become more serious as the use amount of the solvent is decreased with a view to improving productivity. Thus there is a limit to improvement in the productive efficiency, and also safety is in question.

The above-described disadvantage, especially the blocking of the reaction pipe system, is not described or suggested in the above-mentioned references concerning the prior arts.

SUMMARY OF THE INVENTION

After earnest study in order to cope with the above disadvantage, the present inventors have surprisingly found that the below-described process enables improvement in the yield, prevention of the blocking in the condenser and improvement in the productivity and in the safety, and have accomplished the present invention.

Therefore the present invention provides a process for preparing a N-substituted maleimide comprising reacting maleic anhydride with a primary amine using both a non-polar solvent and a protic polar solvent in the presence of an acid catalyst.

DESCRIPTION OF THE PREFERRED EMBODIMENTS

The present invention will hereinafter be described in detail with reference to preferred embodiments.

Maleic anhydride as a starting material of the present invention may be any maleic anhydride provided that it is commercially available in industrial circles. Use of maleic acid in the reaction of the present invention, though possible, requires additional step such as dehydration with heat and therefore is not preferable from the economical point of view.

The primary amine may be any primary amine provided that it is capable of reacting with maleic anhydride to produce a N-substituted maleimide. Examples of the primary amines include aromatic or aliphatic primary amines, specifically aliphatic primary amines such as methylamine, ethylamine, propylamine, butylamine, hexylamine, decylamine, dodecylamine,benzylamine, cyclohexylamine, allylamina and ethylenediamine, and aromatic primary amines such as aniline, toluidine, xylidine, ethylaniline, diethylaniline, anthranilic acid, aminophenol, chloroaniline, dichloroaniline, bromoaniline, dibromoaniline, tribromoaniline and nitroaniline.

As the acid catalyst, sulfuric acid, p-toluenesulfonic acid, orthophosphoric acid, metaphosphoric acid, pyrophosphoric acid, benzenesulfonic acid, methanesulfonic acid and acidic ion-exchange resins may be used. These acid catalysts may be used as a mixture of two or more. Among these acid catalysts, p-toluenesulfonic acid and benzenesulfonic acid are particularly preferred.

The non-polar solvent used in the reaction may be any non-polar solvent provided that it is insoluble in water and does not interfere the reaction. Examples of the non-polar solvents are aromatic hydrocarbons such as benzene, toluene, xylene, ethylbenzene and propylbenzene, aliphatic hydrocarbons such as hexane, heptane, octane and decane, and alicyclic hydrocarbons such as cyclohexane. The choice of the kind of solvent and the usage amount thereof may be decided as appropriate on account of smooth reaction and objective economical. Among these non-polar solvents, xylene and toluene are generally preferred.

As the protic polar solvent, formic acid, acetic acid and propionic acid are preferred, among which acetic acid is particularly preferred.

In the process of the present invention, both the above-mentioned non-polar solvent and protic polar solvent are used. The use ratio of the protic polar solvent with respect to the non-polar solvent is 1 to 20 wt %, preferably 5 to 15 wt % and more preferably 6 to 9 wt %. Additionally, the protic polar solvent may be all mixed before being put into the reaction system, or may be continuously or intermittently added during the reaction.

According to the present invention, the N-substituted maleimide may preferably be produced, for example, by single-step reaction in which maleic anhydride is reacted with the primary amine in the presence of the acid catalyst and the protic polar solvent under reflux of the non-polar solvent with simultaneous removal of generated water. This single-step process is preferable from the view point of productive efficiency.

The N-substituted maleimides may preferably be produced as follows.

The usage amount of maleic anhydride is preferably 0.8 to 1.5 moles, more preferably 0.9 to 1.3 moles, with respect to one mole of the primary amine. When the amount of maleic anhydride is less than 0.8 moles, more addition products of the amine are generated. Thus the purity and the yield of the object product are lowered, unpreferably. When the usage amount of maleic anhydride is more than 1.5 moles, an excess of maleic anhydride results in blocking in the pipe system and is not economically desirable, unpreferably.

The usage amount of the acid catalyst is preferably 0.01 to 0.3 moles, more preferably 0.05 to 0.2 moles, with respect to one mole of the primary amine. When the amount is less than 0.01 moles, the catalytic effect thereof can hardly seen unpreferably. When the amount is more than 0.3 moles, side reactions are promoted and therefore the yield of the object product is lowered.

The reaction temperature, though it varies depending on the kind of major solvent, i.e., the kind of non-polar solvent, is 80° to 200° C., preferably 120° to 160° C. When the reaction temperature is within this range, water generated during the reaction can easily be removed by azeotropic distillation, thereby the reaction rate being improved. For some kinds of major solvents to be employed, the temperature in the reaction system may not reach the above-mentioned range. In such cases, an appropriate temperature is set by adjusting the pressure in the reaction system. For example, in case where a solvent having a low boiling point such as hexane and cyclohexane is used, the reaction may be carried out under pressure. On the other hand, it may be carried out under reduced pressure when a solvent having a high boiling point such as diethylbenzene is used.

The process for preparing the N-substituted maleimide is above explained in accordance with the single-step reaction, but the N-substituted maleimide may be produced by two-step reaction in which maleic anhydride is reacted with the primary amine to produce a maleic acid monoamide in the first step.

In the process of the present invention, the use of both the non-polar solvent and the protic polar solvent is considered to have the following effects:

(1) The protic polar solvent, volatilizing, reduces the partial pressure of maleic anhydride in the gas phase, and accordingly reduces the concentration of maleic anhydride in the gas phase. Thereby the amount of deposits in the pipes decreases and the reaction with the primary amine to generate by-products is prevented.

(2) The protic polar solvent, volatilizing, dissolves and removes deposits in the condenser and the water separator, which prevents the generation of the by-products. This contributes to the yield improvement.

Therefore, compared with the conventional process by use of the non-protic polar solvent such as N,N-dimethylformamide (DMF) in addition to the non-polar solvent, the usage amount of the non-polar solvent is reduced to half to one-third in the present invention. Thus the volume efficiency in the present invention is approximately twice as good as that in the conventional process.

Further, according to the present invention, since generated water during the reaction is removed efficiently by azeotropic distillation, maleic anhydride of the starting material is kept from reacting with water in the reaction system to produce maleic acid. This avoids loss of maleic anhydride, and thereby the purity and the yield are improved in addition to the above-mentioned volume efficiency.

In order to improve productivity, it is possible to further decrease the usage amount of the non-polar solvent. However, accompanying by-production of polymeric products cannot sometimes be by-passed. In such cases, a polymerization inhibitor may preferably be added.

As the polymerization inhibitor, hindered phenols and organic or inorganic copper compounds are suitable.

Examples of the hindered phenols are 2,6-di-t-butyl-p-cresol, 2,5-di-t-butylhydroquinone, 2,5-di-t-amylhydroquinone, 4,4'-butylidenebis(6-t-butyl-3-methylphenol), 2,2'-methylenebis(4-methyl-6-t-butylphenol), and 2,2'-methylenebis(4-ethyl-6-t-butylphenol).

Examples of the copper compounds are metallic copper, copper oxide, copper hydroxide, copper sulfide, copper chloride, copper sulfate, copper nitrate, copper phosphate, copper acetate, copper glycolate, copper propionate, copper valerate, copper citrate, copper hexanoate, copper gluconate, copper salicylate, copper octanoate, copper pelargonate, copper sebacate, copper palmitate, copper oleate, copper stearate, bis(glycinato)copper, bis(acetylacetonato)copper, bis(o-aminobenzenesulfonato)copper, bis(leucinato)copper, bis(acetylacetonato)copper, and copper dibutyldithiocarbamate. These polymerization inhibitors may be added as a mixture of two or more thereof.

The reaction mixture containing a N-substituted maleimide as obtained above may be further neutralized with a diluted alkali solution and washed with water. Then the solvent is removed. And, by distillation, the N-substituted maleimide of higher purity may be obtained.

The process of the present invention is useful for preparing a variety of N-substituted maleimides from maleic anhydride and any primary amine. Particularly the process is preferably employed for preparing N-benzylmaleimide, N-cyclohexylmaleimide, N-phenylmaleimide and N-laurylmaleimide.

The N-substituted maleimides produced by the process of the present invention can be used as materials for medicines, agricultural chemicals, dyes and polymers and as intermediates thereof.

The present invention will hereinafter be described in detail with reference to the following examples, which is not intended to limit the scope of the present invention.

In the present invention, conversion yield, conversion yield ratio and volume efficiency were calculated as follows.

Conversion Yield: The each purity of initial, main and end fractions of a distillation was determined by gas chromatography, respectively. The Conversion Yield was obtained by multiplying the each purity mentioned above by the weight of each of the fractions, and summing all the calculated products.

Conversion Yield Ratio: Conversion Yield Ratio was calculated from the following formula;

$$\text{Conversion Yield Ratio} = \frac{A}{B} \times 100(\%)$$

, wherein A represents the Conversion Yield of the N-substituted maleimides, B represents theoretical yield of N-substituted maleimides on the basis of amine.

Volume Efficiency: Volume Efficieny was calculated from the following formula;

$$\text{Volume Efficiency} = \frac{C}{D+E+F+G+H+I+J} \times 100(\%)$$

, wherein C represents the Conversion Yield, D, E, F, G, H, I and J represent the volume of maleic anhydride, benzylamine, cyclohexylamine, aniline, toluene, acetic acid and formic acid respectively which was calculated by dividing the weight by their specific gravities.

Referring to tables 1 and 2, in ranks regarding blocking states of the condenser and the water separator, the sign of ○ indicates that no or little deposit was observed, △ indicates that some deposit was observed, and X indicates that a lot of deposit was observed and also that the pipes were blocked.

EXAMPLE 1

Prepared was a one-liter glass reactor provided with an stirrer, a thermometer, a dropping funnel as well as a evaporator for dehydration, a condenser and a water separator. Into this reactor, 420 g of xylene and 57 g of p-toluenesulfonic acid were put as acid catalyst, and the water separator was filled with xylene.

First, water of crystallization of p-toluenesulfonic acid was removed under reflux of xylene and then the reactor was cooled to a temperature at which xylene was not refluxed any longer.

Then, 176.6 g of maleic anhydride (1.8 moles), 0.28 g of 2,2'-methylenebis(4-methyl-6-t-butylphenol) as polymerization inhibitor A, and 4.5 g of acetic acid were put into the reactor.

The mixture was heated to reflux xylene. The temperature was 137° C. When xylene became refluxed at regular reflux rate, 160.8 g of benzylamine (1.5 moles) were added in 3 hours, while generated water was successively removed out of the reaction system by the water separator. Then the mixture was heated for an hour for completion of the reaction. The reaction mixture containing N-benzylmaleimide was obtained. The temperature was 146° C. During the reaction, the condenser was never blocked or the water separator was never fouled inside.

The reaction product in the reaction mixture was analyzed by gas chromatography in accordance with the internal standard method and the reaction ratio was found to be 85.3% on the basis of benzylamine.

Then, the reaction product was washed with 280 g of water at 75° C. and the aqueous layer was removed. Then the acid value of the content in the reactor then was 2.5. Then, 280 g of sodium carbonate ($Na_2CO_3$) (one and half times of the above acid value equivalent) were solved in 280 g of water at 75° C., and added into the product phase for neutralization. The mixture was washed with another 280 g of water at 75° C. to complete after-treatment.

Then, xylene was distilled off under reduced pressure of 10 mmHg at 140° C. The gross yield at this stage was 253.1 g (the gross yield ratio being 90.1%). Two hundred fifty one point two grams (251.2 g) of this unpurified product was further subjected to simple distillation in vacuo of 2 mmHg to obtain 7.5 g of initial fraction of the distillation, 210.9 g of main fraction of the distillation, 16.5 g of end fraction of the distillation and 16.3 g of residue.

All the fractions were analyzed by gas chromatography to obtain the conversion yield, 230.0 g. The conversion yield ratio was 81.9%. The purity of the main fraction determined by gas chromatography was 99.8%. The results were shown in Table 1.

EXAMPLES 2 TO 4

Using the reactor as described in Example 1, the same procedure as taken in Example 1 was repeated except that the use amounts of xylene and acetic acid were changed as shown in Table 1. In Examples 3 and 4 in which the use amount of the non-polar solvent is considerably decreased, 0.28 g of copper dibutyldithiocarbamate was added as polymerization inhibitor B. The results are shown in Table 1.

EXAMPLES 5 TO 7

Using the reactor as described in Example 1, the same procedure as taken in Example 1 was repeated except that cyclohexylamine was used in place of the primary amine to produce N-cyclohexylmaleimide. The results are shown in Table 1.

EXAMPLES 8 TO 9

The procedures in Examples 4 and 7 were repeated except that formic acid was used in place of acetic acid. The results are shown in Table 1.

EXAMPLE 10

The procedure in Example 4 was repeated except that aniline, toluene and polymerization inhibitor A were used in place of benzylamine, xylene and polymerization inhibitor B respectively to produce N-phenylmaleimide. The results were shown in Table 1.

TABLE 1

|  | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|
| Maleic Anhydride | 176.6 | 176.6 | 176.6 | 176.6 | 176.6 | 176.6 | 176.6 | 176.6 | 176.6 | 176.6 |
| (mol) | 1.8 | 1.8 | 1.8 | 1.8 | 1.8 | 1.8 | 1.8 | 1.8 | 1.8 | 1.8 |
| Benzylamine | 160.8 | 160.8 | 160.8 | 160.8 |  |  |  | 160.8 |  |  |
| (mol) | 1.5 | 1.5 | 1.5 | 1.5 |  |  |  | 1.5 |  |  |
| Cyclohexylamine |  |  |  |  | 148.5 | 148.5 | 148.5 |  | 148.5 |  |
| (mol) |  |  |  |  | 1.5 | 1.5 | 1.5 |  | 1.5 |  |
| Aniline |  |  |  |  |  |  |  |  |  | 139.5 |
| (mol) |  |  |  |  |  |  |  |  |  | 1.5 |
| Solvent |  |  |  |  |  |  |  |  |  |  |
| Xylene (g) | 420.0 | 278.0 | 195.0 | 135.0 | 278.0 | 195.0 | 135.0 | 135.0 | 135.0 |  |
| Toluene (g) |  |  |  |  |  |  |  |  |  | 135.0 |
| Acetic Acid (g) | 4.5 | 7.5 | 10.5 | 21.0 | 7.5 | 10.5 | 21.0 |  |  | 21.0 |
| Formic Acid (g) |  |  |  |  |  |  |  | 21.0 | 21.0 |  |
| Polymerization Inhibitor | A | A | B | B | A | B | B | B | B | A |
| Reaction Ratio (%) | 85.3 | 86.6 | 87.3 | 87.9 | 83.2 | 84.4 | 84.6 | 88.0 | 83.8 | 97.1 |
| Conversion Yield Ratio (%) | 81.9 | 82.1 | 84.5 | 84.4 | 80.0 | 79.1 | 80.3 | 82.9 | 80.5 | 94.9 |
| Conversion Yield (g) | 230.0 | 230.7 | 237.4 | 237.1 | 214.8 | 212.4 | 215.6 | 232.9 | 216.1 | 246.6 |
| Volume Efficiency (%) | 0.30 | 0.38 | 0.46 | 0.52 | 0.34 | 0.40 | 0.46 | 0.51 | 0.46 | 0.58 |
| Appearance | white crystal | white crystal | white crystal | white crystal | white crystal | white crystal | white crystal | white crystal | white crystal | white crystal |
| Purity of the Product (%) | 99.8 | 99.9 | 99.8 | 99.7 | 99.9 | 99.9 | 99.8 | 99.8 | 99.9 | 99.9 |
| Blocking Condenser | o | o | o | o | o | o | o | o | o | o |
| Water Separator | o | o | o | o | o | o | o | o | o | o |

Polymerization Inhibitor A: 2,2'-methylenebis(4-methyl-6-t-butylphenol)
B: Copper dibutyldithiocarbamate

COMPARATIVE EXAMPLE 1

The same procedure as described in Example 1 was repeated except that 21.9 g of N,N-dimethylformamide (DMF) was used in place of acetic acid.

In Examples 1 to 10, neither deposits in the condenser nor crystalline substances in the water separator were observed.

In Comparative Example 1, however, deposits were found in the condenser and the water separator about 30 minutes after benzylamine was added.

Further, during 3 hours to the completion of the whole reaction, these deposits gradually accumulated. The composition of the deposits was analyzed by liquid chromatography, and they were observed to contain 45% maleic acid monobenzylamide, 53.5% maleic acid and 1.5% N-benzylmaleimide.

The content in the reactor was analyzed by gas chromatography according to the internal standard method, and the reaction ratio was found to be 82.5%. This content was then subjected to the after-treatment and the distillation as described in Example 1. The gross yield was 240.2 g (the gross yield ratio being 85.5%). Two hundred thirty-seven point seven grams (237.7 g) of this product was further subjected to distillation to obtain 7.3 g of fraction at the initial boiling, 192.3 g of fraction at the main boiling, 15.5 g of fraction at the stop boiling and 23.1 g of residue.

All the fractions were analyzed by gas chromatography to obtain the conversion yield, 210.2 g. The conversion yield ratio was 74.8%. The purity of the main fraction determined by gas chromatography was 99.8%, which was not different from that of Example 1. The results were shown in Table 2.

COMPARATIVE EXAMPLES 2 TO 3

The procedures in Examples 4 and 7 were repeated without using acetic acid. The results are shown in Table 2.

In these comparative examples, the condenser was blocked and the inside of the water separator was fouled immediately after the primary amine was added. Thus, the reactor had to be cleaned during the reaction, and, after the cleaning, the procedures were resumed to be completed. The results are shown in Table 2.

TABLE 2

|  | Comparative Ex. 1 | Comparative Ex. 2 | Comparative Ex. 3 |
|---|---|---|---|
| Maleic Anhydride | 176.6 | 176.6 | 176.6 |
| (mol) | 1.8 | 1.8 | 1.8 |
| Benzylamine | 160.8 | 160.8 |  |
| (mol) | 1.5 | 1.5 |  |
| Cyclohexylamine |  |  | 148.5 |
| (mol) |  |  | 1.5 |
| Solvent |  |  |  |
| Xylene (g) | 420.0 | 135.0 | 135.0 |
| DMF (g) | 21.9 | 21.9 | 21.9 |
| Polymerization Inhibitor | A | B | B |
| Reaction Ratio (%) | 82.5 | 79.9 | 78.1 |
| Conversion Yield Ratio (%) | 74.8 | 70.4 | 69.3 |
| Conversion Yield (g) | 210.2 | 197.8 | 186.1 |
| Efficiency By Volume (%) | 0.27 | 0.43 | 0.39 |
| Appearance | white crystal | white crystal | white crystal |
| Purity of the Product (%) | 99.8 | 99.6 | 99.8 |
| Blocking |  |  |  |
| Condenser | Δ | X | X |
| water Separator | Δ | X | X |

DMF: N,N-dimethyl formamide

It is clear from the above Tables 1 and 2 that, according to the present invention, the reaction ratio is improved and the by-products deposited in the condenser and the water separator such as maleic acid and maleic acid monoamide are prevented from blocking the reaction apparatus.

According to the process of the present invention, the evil effects due to decrease in use amount of the organic solvent with the view of raising industrial productivity, that is, problems in industrial production such as the increase of by-products with the primary amine caused by high concentration of maleic anhydride in the gas phase and the blocking of the condenser and the like are avoided because the protic polar solvent dissolves the by-products which will otherwise deposit in the apparatus. Further, since the protic polar solvent dissolves maleic anhydride and maleic acid and return them in the reaction system, loss of maleic anhydride is reduced and the N-substituted maleimide of high purity can be obtained in high yield.

What is claimed is:

1. A process for preparing a N-substituted maleimide comprising reacting maleic anhydride with a primary amine using both a non-polar solvent and a protic polar solvent in the presence of an acid catalyst and a polymerization inhibitor.

2. A process for preparing a N-substituted maleimide according to claim 1 wherein the primary amine is selected from the group consisting of methylamine, ethylamine, propylamine, butylamine, hexylamine, decylamine, dodecylamine, benzylamine, cyclohexylamine, allylamine, ethylenediamine, aniline, toluidine, xylidine, ethylaniline, diethylaniline, anthranilic acid, aminophenol, chloroaniline, dichloroaniline, bromoaniline, dibromoaniline, tribromoaniline and nitroaniline.

3. A process for preparing a N-substituted maleimide according to claim 1 wherein maleic anhydride is used in an amount of 0.8 to 1.5 moles with respect to one mole of the primary amine.

4. A process for preparing a N-substituted maleimide according to claim 3 wherein maleic anhydride is used in an amount of 0.9 to 1.3 moles with respect to one mole of the primary amine.

5. A process for preparing a N-substituted maleimide according to claim 1 wherein the non-polar solvent is xylene or toluene.

6. A process for preparing a N-substituted maleimide according to claim 1 wherein the protic polar solvent is selected from formic acid, acetic acid and propionic acid.

7. A process for preparing a N-substituted maleimide according to claim 1 wherein the ratio of the protic polar solvent with respect to the non-polar solvent is 1 to 20 wt %.

8. A process for preparing a N-substituted maleimide according to claim 7 wherein the ratio of the protic polar solvent with respect to the non-polar solvent is 5 to 15 wt %.

9. A process for preparing a N-substituted maleimide according to claim 8 wherein the ratio of the protic polar solvent with respect to the non-polar solvent is 6 to 9 wt %.

10. A process for preparing a N-substituted maleimide according to claim 1 wherein the acid catalyst is at least one selected from the group consisting of sulfuric acid, para-toluenesulfonic acid, orthophosphoric acid, metaphosphoric acid, pyrophosphoric acid, benzenesulfonic acid, methanesulfonic acid and acidic ion-exchange resins.

11. A process for preparing a N-substituted maleimide according to claim 1 wherein the acid catalyst is used in an amount of 0.01 moles to 0.3 moles with respect to the primary amine.

12. A process for preparing a N-substituted maleimide according to claim 11 wherein the acid catalyst is used in an amount of 0.05 moles to 0.2 moles with respect to the primary amine.

13. A process for preparing a N-substituted maleimide according to claim 1 wherein the reaction is carried out at a temperature within the range from 80° C. to 200° C.

14. A process for preparing a N-substituted maleimide according to claim 13 wherein the reaction is carried out at a temperature within the range from 120° C. to 160° C.

15. A process for preparing a N-substituted maleimide according to claim 1 wherein the polymerization inhibitor is selected from the group consisting of 2,6-di-t-butyl-p-cresol, 2,5-di-t-butylhydroquinone, 2,5-di-t-amylhydroquinone, 4,4'-butylidenebis(6-t-butyl-3-methylphenol), 2,2'-methylenebis(4-methyl-6-t-butylphenol), 2,2'-methylenebis(4-ethyl-6-t-butylphenol), metallic copper, copper oxide, copper hydroxide, copper sulfide, copper chloride, copper sulfate, copper nitrate, copper phosphate, copper acetate, copper glycolate, copper propionate, copper valerate, copper citrate, copper hexanoate, copper gluconate, copper salicylate, copper octanoate, copper pelargonate, copper sebacate, copper palmitate, copper oleate, copper stearate, bis(glycinato)copper, bis(acetylacetonato)copper, bis(o-aminobenzenesulfonato), bis(leucinato)copper, bis(acetylacetonato)copper, and copper dibutyldithiocarbamate.

* * * * *